United States Patent [19]

Brumfield

[11] Patent Number: 4,827,917
[45] Date of Patent: May 9, 1989

[54] FERMORAL FRACTURE DEVICE

[75] Inventor: David L. Brumfield, Nesbit, Miss.

[73] Assignee: Richards Medical Company, Memphis, Tenn.

[21] Appl. No.: 947,656

[22] Filed: Dec. 30, 1986

[51] Int. Cl.⁴ ............................................... A61F 5/04
[52] U.S. Cl. ............................. 128/42 YZ; 128/92 YY
[58] Field of Search ......... 128/92 YZ, 92 YY, 92 YV

[56] References Cited

U.S. PATENT DOCUMENTS

| | | | |
|---|---|---|---|
| 4,281,649 | 8/1981 | Derweduwen | 128/92 YZ |
| 4,473,069 | 9/1984 | Kolmert | 128/92 YZ |
| 4,522,202 | 6/1985 | Otte et al. | 128/92 YZ |
| 4,622,959 | 11/1986 | Marcus | 128/92 YZ |
| 4,667,664 | 5/1987 | Taylor et al. | 128/92 YY |

FOREIGN PATENT DOCUMENTS

| | | | |
|---|---|---|---|
| 118778 | 9/1984 | European Pat. Off. | 128/92 YY |
| 2160775 | 1/1986 | United Kingdom | 128/1 R |

OTHER PUBLICATIONS

Brochure entitled Russell—Taylor Interlocking Nail System.

Brochure Article (copy) Entitled Naling of Interochanteric Fractures.

Primary Examiner—C. Fred Rosenbaum
Assistant Examiner—Mark F. Colosimo
Attorney, Agent, or Firm—Kirkpatrick & Lockhart

[57] ABSTRACT

An apparatus for treating fractures of the femur including a screw and an intramedullary rod. The screw has a threaded portion and a smooth portion. The rod has a head, stem and a longitudinal bore. There is at least one pair of coaxial holes through the stem, transverse to the longitudinal axis of the rod, for receiving first anchoring means, such as a nail, screw or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw to permit the threaded portion of the screw, in use, to engage the femoral head and to allow sliding compression of a femoral neck or intertrochanteric fracture. An optional second anchoring means which will also allow sliding compression and an optional set screw are also provided to adapt the fracture device to a variety of applications.

10 Claims, 3 Drawing Sheets

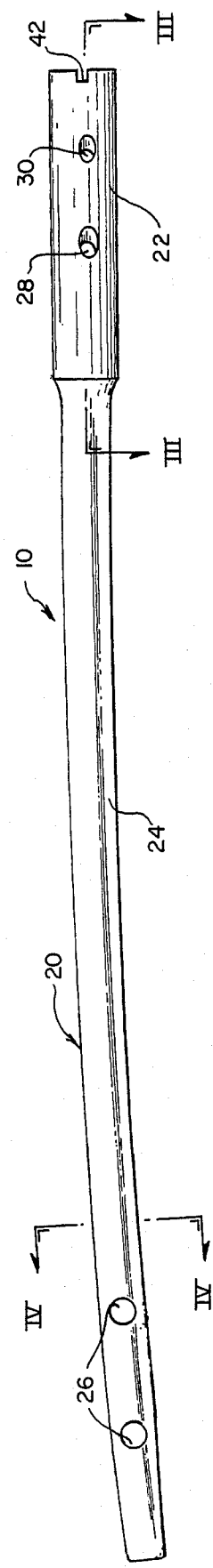
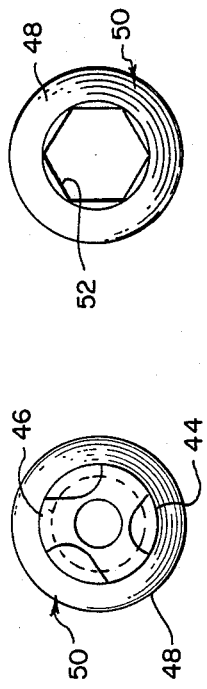
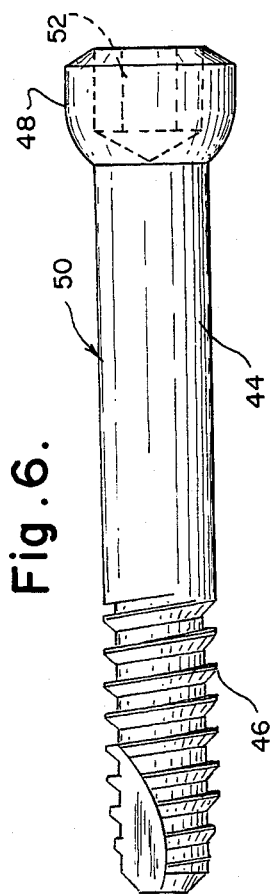
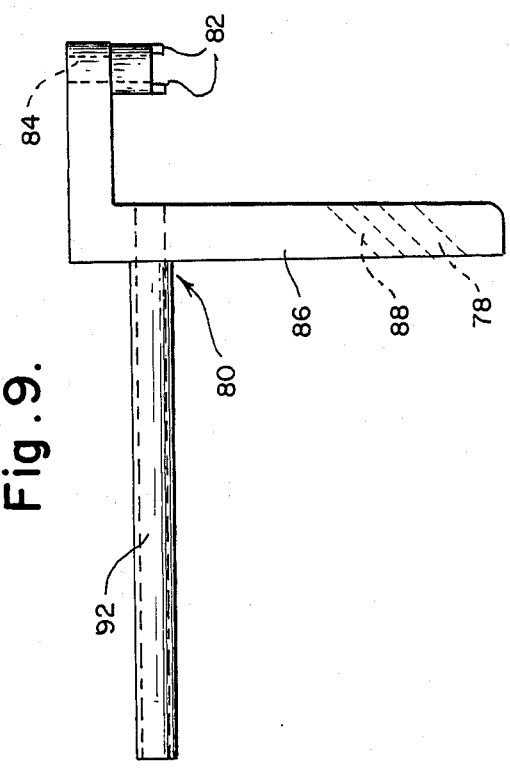

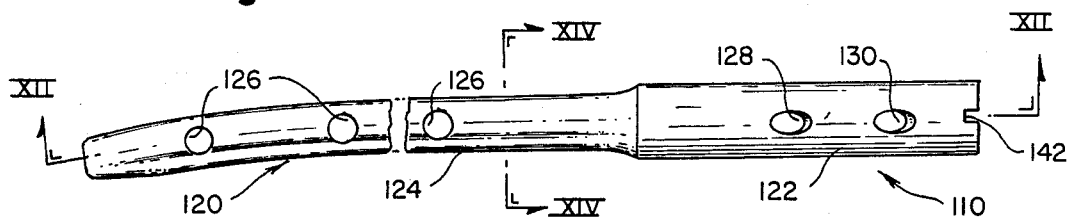
Fig. 11.
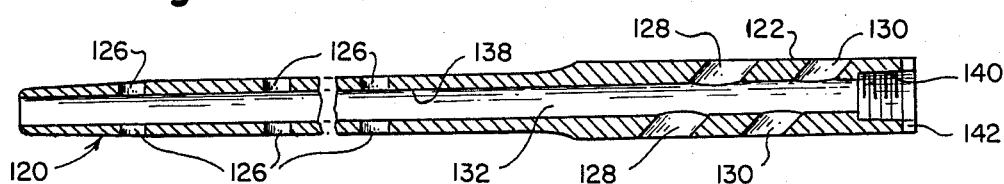
Fig. 12.
Fig. 14. Fig. 13.
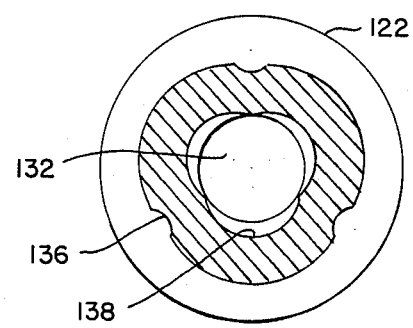
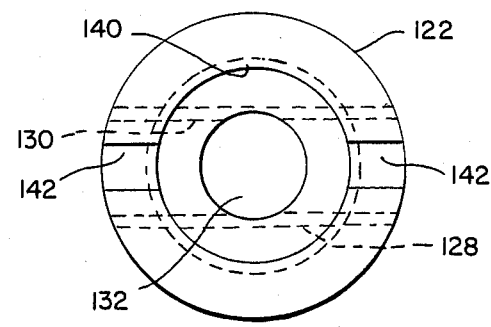
Fig. 10.
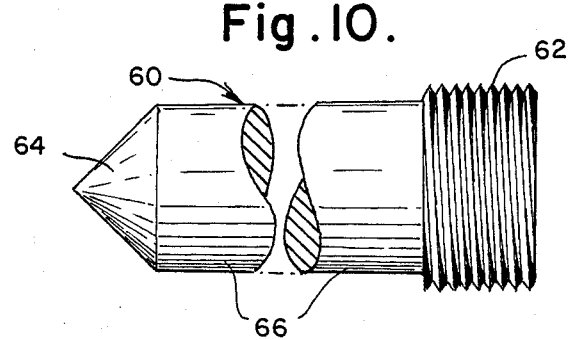

FEMORAL FRACTURE DEVICE

BACKGROUND OF THE INVENTION

1. Field of the Invention

The invention relates generally to devices for treating femoral fractures and, more particularly, to intramedullary rods.

2. Description of the Prior Art

There are a variety of devices used to treat femoral fractures. Fractures of the neck, head or intertrochanter of the femur have been successfully treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw.

Compression screw assemblies are shown by the following patents: Fixel U.S. Pat. No. 4,432,358; Callender, Jr. U.S. Pat. No. 3,374,786; Pugh et al. U.S. Pat. No. 2,702,543; Griggs U.S. Pat. No. 4,530,355; Blosser, U.S. Pat. No. 3,094,120; and Wagner U.S. Pat. No. 3,842,825. The Blosser and Wagner patents illustrate the use of multiple screws to prevent rotation of the lag screw relative to the compression plate and barrel member. A surgical bone pin which functions like a lag screw and compressing screw but which does not include a compression plate is shown by Cochran et al. U.S. Pat. No. 3,103,926.

Subtrochanteric and femoral shaft fractures have been treated with the help of intramedullary rods which are inserted into the marrow canal of the femur to immobilize the femur parts involved in fractures. A single angled cross-nail or locking screw is inserted through the femur and the proximal end of the intramedullary rod. In some varieties, one or two screws may also be inserted through the femoral shaft and through the distal end of the intramedullary rod. The standard intramedullary rods have been successfully employed in treating fractures in lower portions of the femoral shaft.

The Grosse-Kempf nail manufactured by Howmedica Company of Rutherford, New Jersey is believed to be one of the earliest intramedullary nailing devices introduced into the United States. The Grosse-Kempf nail includes a threaded hole in the intramedullary rod for receiving the interlocking screw. The fully threaded screw cannot slide through the threaded hole to permit the type of compression found in the compression screw assemblies discussed above. Furthermore, the axis of the threaded hole coincides with a line between the greater to lesser trochanter and not in the direction of the femoral neck.

Zickel U.S. Pat. No. 3,433,220, which issued on Mar. 18, 1969, discloses an intramedullary rod and cross-nail assembly which is useful in treating fractures occurring in the upper one-third or subtrochanteric portion of the femur. The Zickel nail is a solid intramedullary nail having a single proximal tri-flange cross-nail which is inserted in the direction of the femoral head. The intramedullary rod is curved in two planes to mimic the shape of the femur. The solid cross section does not permit insertion over a guide rod, thus preventing the use of the Zickel nail for comminuted and distal fractures of the femur because the closed surgical technique cannot be practiced. The rigid tri-flange cross-nail is not suitable for use in treating femoral neck fractures because the cross-nail must be locked into position by a set screw to prevent backing out. Adequate compression cannot be achieved. As stated above, the sliding compression screw has been found to be most effective in treating femoral neck fractures.

The commercially available Kuntscher Y-nail includes a flanged cloverleaf shaped intramedullary nail which is inserted through a hole in a single femoral neck nail. The rod includes a longitudinal slit. The Kuntscher device is indicated only for unstable trochanteric fractures. Neither the Kuntscher device, nor the Zickel nail, includes distal anchoring means and both therefore are not useful for treating distal fractures. The femoral neck nail of the Kuntscher device, which is angled toward the femoral neck, is locked into place by the intramedullary rod. Thus, the Kuntscher Y-nail is also not indicated for femoral neck fractures.

The Russell-Taylor interlocking nail system manufactured by Richards Medical Company of Memphis, Tennessee includes an intramedullary rod having two pairs of coaxial holes through its proximal end. The axes of the pairs of holes intersect to provide a left or right orientation for insertion of a single locking screw. The screw is designed to pass from the greater to the lesser trochanter. There is not sufficient mechanical support to allow usage of the locking screw in the direction towards the femoral head because the second pair of coaxial holes weaken the nail when loaded in that direction. Further, the locking screw is a fully threaded screw which does not permit sliding of the screw relative to the intramedullary rod.

Another bone-nail which permits left-right orientation by means of "criss-cross" nail holes is shown by Ender U.S. Pat. No. 4,475,545.

For unstable subtrochanteric fractures, the extreme loads have frequently caused implants, such as hip compression screw plates, to fail. In cases of severe comminution of the femoral shaft, existing interlocking nails have at times not provided adequate strength.

It is an object of the present invention to provide a single device which can be used to treat a variety of fractures. Such a device would permit hospitals to reduce their inventories of orthopaedic surgical devices and thereby reduce costs.

It is a further object of the present invention to provide a device which combines the superior mechanical and biological attributes of intramedullary fixation with the proven benefits of the sliding compression screw for fracture reduction.

It is a further object of the present invention to provide a stronger fracture device which more closely approximates the performance of the unbroken bone.

SUMMARY OF THE INVENTION

The present invention provides an apparatus for treating fractures of the femur which marries the fixation attributes of an intramedullary nail with the proven benefits of the sliding compression screw. The apparatus of the invention provides a single device for treating a variety of femoral fractures, which heretofore have required more than one device. The apparatus comprises a screw and an intramedullary rod. The screw includes a threaded portion adapted in use to engage the head of a femur and a smooth portion for sliding.

The intramedullary rod has a longitudinal axis and defines a coaxial bore therethrough. The bore has a closed cross section along its entire length. The rod also includes a proximal head and a stem distal thereto. The longitudinal axis curves in at least one portion of the stem to align the rod along the length of the marrow canal of the femur when the rod is inserted in the femur. The curve of the longitudinal axis, and thus the curve of the stem of the rod, is through a single plane.

The stem has at least one pair of stem holes at the distal end of the stem. Both holes of the at least one pair of stem holes are coaxially arranged on a common axis extending through the bore of the rod in transverse direction relative to the longitudinal axis of the rod.

The head has at least a distal pair of head holes for slidingly receiving the screw and a proximal pair of head holes. Both holes of each such distal and proximal pairs of head holes are coaxially arranged on a common axis extending through the bore in an angled direction relative to the longitudinal axis of the rod. The common axes of the distal and proximal pairs of head holes are generally parallel to each other.

The apparatus may further include first anchoring means, such as a nail, screw or bolt, adapted in use to pass through the femur and the pair of stem holes to secure the rod within the marrow canal of the femur. There are preferably two pairs of stem holes, the common axes of which are parallel to each other, and thus, preferably, two first anchoring means.

The preferred embodiment of the apparatus includes a second anchoring means adapted in use to be optionally insertable through a portion of the femur and the proximal pair of head holes to prevent rotation of the femoral head. The insertion of the second anchoring means is indicated in treating femoral neck and unstable intertrochanteric fractures. The apparatus also includes a set screw adapted in use to be optionally insertable into that portion of the bore in the head of the intramedullary rod to wedgedly engage the screw when the screw is inserted through the distal pair of head holes to thereby secure the position of the screw relative to the rod. The insertion of the set screw is indicated in treating subtrochanteric or other fractures where only the screw and not the combination of the screw and the second anchoring means is required.

BRIEF DESCRIPTION OF THE DRAWINGS

The present invention can be better understood by reference to the drawings in which:

FIG. 2 is an elevation view of the intramedullary rod of the present invention (right nail is shown);

FIG. 6 is an enlarged elevation view of the screw of the present invention;

FIG. 7 is a top end view of the screw of FIG. 6;

FIG. 8 is a bottom end view of the screw of FIG. 6;

FIG. 9 is a side elevation view of a tool used to align and drive the apparatus of the present invention;

FIG. 10 is a set screw of the present invention;

FIG. 11 is an alternative embodiment of the intramedullary rod of the present invention;

FIG. 12 is a cross section view of the intramedullary rod of FIG. 11 taken through the lines XII—XII;

FIG. 13 is a top end view of the intramedullary rod of FIG. 11; and

FIG. 14 is a cross section view of the stem of the intramedullary rod of FIG. 11 taken through the line XIV—XIV.

DETAILED DESCRIPTION OF THE PREFERRED EMBODIMENTS

Figure 1:
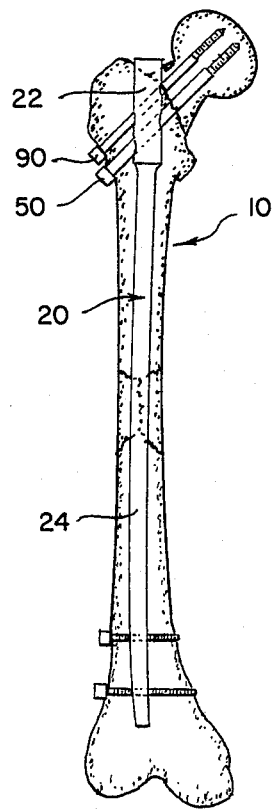
FIG. 1 is a view of the intramedullary rod of the present invention in place in a femur (several fracture patterns shown)

FIGS. 1 through 14 illustrate the preferred embodiments of the femoral fracture device 10 of the present invention.

The femoral fracture device 10 includes intramedullary rod 20, lag screw 50, optional set screw 60 and an optional additional anchoring means 90. The device may be made of any suitable strong, biocompatible material but stainless steel, titanium or chrome-cobalt are preferred. A tool 80 used for aligning the rod 20, lag screw 50 and the optional additional anchoring means 90 is shown in FIG. 9.

Intramedullary rod 20 includes a proximal head 22, a stem 24 distal to the head 22 and a longitudinal bore 32. Referring to FIG. 2, the longitudinal axis of rod 20 curves through one plane along the stem 24 to align the rod along the length of the marrow canal of the femur.

Figure 3:
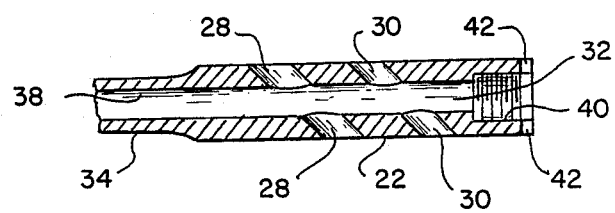
FIG. 3 is a cross section of the head of the intramedullary rod of FIG. 2 taken through the line III—III.
Figure 5:
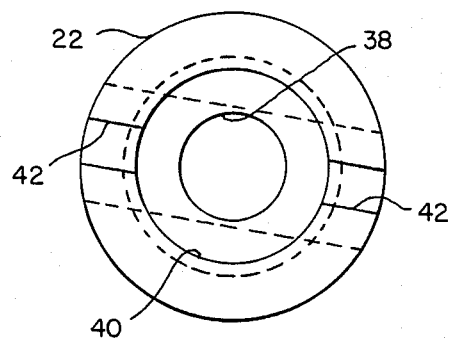
FIG. 5 is a top end view of the intramedullary rod of FIG. 2.

The head 22 includes at least two pairs of holes, a proximal pair of holes 30 and a distal pair of holes 28. Referring to FIG. 3, the holes of a pair are coaxially arranged on a common axis extending through bore 32 in an angled direction relative to the longitudinal axis of rod 20. The common axes of the distal and proximal pairs of holes 28 and 30, respectively, are generally parallel to each other. The diameter of the distal pair of holes 28 is preferably greater than the diameter of the proximal pair of holes 30. The surface of rod 20 which defines the holes 28 and 30 is smooth to permit sliding contact with lag screw 50 and optional additional anchoring means 90 for sliding compression of a femoral neck or intertrochanteric fracture. A threaded counterbore 40 with slots 42 is provided at the end of head 22 to receive the set screw 60 and prongs 82 of tool 80, respectively. The axis of slots 42 is parallel in one plane with the common axes of holes 28 and 30 to insure alignment with tool 80. Axes of both slots 42 and holes 28 and 30 may be angled (as shown in FIG. 5) with respect to the plane containing the curve of stem 24 to position screw 50 in the same anteverted direction of the normal femoral head.

Stem 24 includes at least one, and preferably two pairs of holes 26. Both holes of a pair of holes 26 are coaxially arranged on a common axis extending through the bore 32 in a transverse, preferably perpendicular, direction relative to the longitudinal axis of the rod 20. Holes 26 are adapted to receive any suitable known anchoring means (not shown), such as nails, screws or bolts to secure rod 20 within the marrow canal of the femur. Distal anchoring provided by holes 26 prevents shortening and rotation of unstable shaft-fractures.

Figure 4:
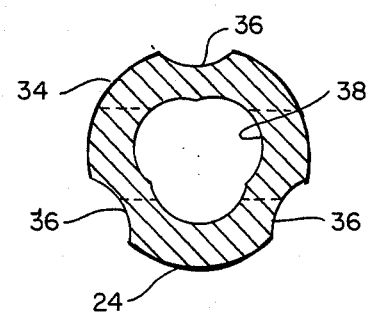
FIG. 4 is a cross section view of the stem of the intramedullary rod of FIG. 2 taken through the line IV—IV.

The stem 24, as shown in FIG. 4, resembles a clover leaf in shape. The interior surface 38 of rod 20 is also clover-leaf shaped. The exterior surface 34 of stem 24 is defined by three arcs separated from each other by scalloped sections 36. The scalloped surface provides space surrounding the rod 20 for the endosteal blood supply. A sufficient flow of blood throughout the region is necessary to promote healing.

The closed cross sectional construction of rod 20 provides approximately a ten fold increase in torsional strength over the variety of prior art rods having an open cross-section formed by a slit along the length of the rod. It is known that the rods having such a longitudinal slit have experienced torsional problems. The rods can twist causing malalignment of bone segments and improper healing due to the excess shearing motion at the fracture site. The cross section of the rod 20 of the present invention is closed and is thicker than conventional rods, thereby providing a stronger construction with greater torsional stability for application in treating subtrochanteric and highly comminuted fractures.

Referring to FIG. 6, the lag screw 50 includes a smooth portion 44, a self-tapping threaded end 46 and a beveled head portion 48. A hexagonally shaped inset 52 in the head portion 48 permits insertion of a suitable tool for compression of lag screw 50. Lag screw 50 is preferably cannulated to permit insertion of a guide wire. The optional anchoring means 90 is of similar construction to permit sliding compression. Anchoring means 90 shown in FIG. 1 has a threaded portion and a smooth portion.

The set screw 60, shown in FIG. 10, has a threaded portion 62, a shaft 66 and a beveled tip 64. The set screw 60 is preferably long enough to wedgedly engage the smooth portion 44 of lag screw 50 when lag screw 50 is inserted through the distal pair of holes 28 in head 22 of rod 20. The set screw 60 secures lag screw 50 in position relative to rod 20. Counterbore 40 is preferably deeper than threaded portion 62 of set screw 60 and the shaft 66 of set screw 60 is preferably longer than that portion of bore 32 in head 22 into which the set screw is inserted prior to contacting lag screw 50 so that sufficient pressure can be applied to set screw 60 to wedge it securely against lag screw 50.

A tool 80 is shown in FIG. 9 to help align the parts of femoral fracture device 10 during application to a patient. The tool 80 includes prongs 82 to engage slots 42 of head 22 to align bore 84 with bore 32 for insertion of a (temporary) cannulated locking bolt therethrough to secure tool 80 to rod 20 for driving and for precise alignment of drilling instruments and lag screws..

By placing prongs 82 in slots 42, bores 88 and 78 of arm 86 of tool 80 align with the proximal and distal pairs of holes 30 and 28, respectively, of head 22. Lag screw 50 and the optional additional anchoring means can be inserted through the appropriate holes in rod 20 by means of tool 80. Tool 80 also includes a handle 92 for manipulating rod/tool assembly while driving into the bone marrow cavity. Handle 92 contains a keyway for attachment and alignment of a distal targeting device for aligning distal locking screws through holes 26 of rod 20.

An alternative embodiment of the femoral fracture device 110 is shown in FIGS. 11 and 12. Rod 120 may be of varying length for use in simple femoral neck fractures. There is no need to ream the entire length of the femoral marrow channel if there is no trauma to the region. FIG. 11 illustrates a shorter rod 120 having bore 132, a head 122 and a stem 124. Head 122 has proximal and distal pairs of holes 130 and 128, respectively, oriented in the same manner as the corresponding holes 30 and 28 in the longer version of rod 20 described above.

The shorter stem 124 of rod 120 has shown three pairs of holes 126 along its length. The holes 126 are oriented in the same manner as the corresponding holes 26 in stem 24 of rod 20. There may be any number of such paired holes to accommodate different needs. At least one pair of holes 126, however, is recommended.

The femoral fracture device 10, or the alternative embodiment 110, may be inserted into a patient using a known closed intramedullary surgical technique which requires minimal exposure of the femur. Image intensification equipment is employed to guide the surgeon during the procedure.

The fracture device 10, 110, may be inserted into the patient by any suitable known technique. Generally, the marrow canal of the femur is first reamed with an appropriate known reaming tool to create a void for insertion of the rod 10, 110. Progressively larger reamers are used to increase the diameter of the void. As stated above, when the shorter version 110 of the device is used, the reaming need not be very deep. The voided area within the marrow canal should be over reamed to accommodate different sized patients and to permit sufficient space for blood flow after insertion of the rod 20, 120. It is recommended that the bore be over reamed by at least one mm. A guide pin or wire is inserted into the reamed area. Then the rod 20, 120, is guided into the reamed marrow canal of the femur. The internal bore 32 of rod 20 is necessary for driving the nail over a previously inserted guide rod which served to align the displaced fracture and guide a series of flexible cannulated reamers for preparing the narrow cavity to accept stem 24. The position of the rod 20, 120 including the orientation of the holes should be verified by image intensification.

When the rod is properly oriented, the tool 80 can be used to align the lag screw 50 with the distal pair of holes 28, 128 of head 22, 122. Prior to insertion of lag screw 50, the area must be appropriately reamed by known techniques. A hole in the femoral head and neck is prepared to accept lag screw 50 with a "step-drill" or "step-reamer" containing two diameters: a smaller diameter at its tip corresponding to the root diameter of the lag screw thread; and a larger diameter which is equal to the diameter of the smooth portion of lag screw 50. This preparation allows lag screwing the femoral head and thus sliding compression of a femoral neck fracture. A guide wire is used to determine proper position of lag screw 50 in the femoral head. Lag screw 50 is inserted through a sleeve which fits snugly into bore 78 of tool 80 and into holes 28, 128. The threaded end 46 engages the femoral head. The smooth portion 44 slides through holes 28, 128. A hexagonal screwdriver or any suitable tool can be used to compress lag screw 50 to a desired degree.

If there is a femoral neck fracture the compression of lag screw 50 functions like a compression screw assembly to reduce the fracture. Anchoring means 90 is then optionally inserted through a sleeve which fits snugly into bore 88 of tool 80 into the proximal pair of holes 30, 130 in head 22, 122. The insertion of the optional anchoring means 90 is indicated in femoral neck fractures and unstable intertrochanteric fractures to prevent rotation of the femoral head and to provide auxiliary support to proximal bone fragments. The area is reamed in an appropriate manner prior to insertion of the optional anchoring means 90.

If the optional anchoring means 90 is not needed, for example in a subtrochanteric fracture, then the optional set screw 60 is inserted through bore 84 of tool 80 into that portion of bore 32, 132 in head 22, 122 of rod 20, 120 until the beveled tip 64 wedges against the smooth portion 44 of lag screw 50 to jam the lag screw 50 against holes 28, 128 to secure lag screw 50 relative to rod 20, 120. The threaded portion 62 of set screw 60 is tightened into the threaded portion of counterbore 40, 140 until the lag screw 50 is secure.

Image intensification equipment is used to locate and determine the orientation of holes 26, 126 for insertion of suitable known anchoring means, such as nails, screws or bolts. The insertion of the distal anchoring means in the stem of rod 20, 120 is indicated in unstable shaft fractures.

Removal of the rod 20, 120 is less traumatic than removal of some varieties of known intramedullary nailing devices because the rod 20, 120 is curved in only one plane. Although the femur is naturally curved in more than one plane, the removal of a rod which mimics the curves of the natural femur can cause trauma to the femur and, on occasion, can break the bone.

The femoral fracture device 10 of the present invention is biomechanically a superior method of treating a wide range of femoral fracture patterns, such as combination neck/shaft fractures, any type of femoral neck fracture, certain intertrochanteric fractures, subtrochanteric fractures, severely comminuted shaft fractures, reconstruction of the femoral shaft, allograft reconstruction of the femoral shaft after tumor resection, and leg lengthening. Other uses will be recognized by those skilled in the art.

What is claimed is:

1. Apparatus for treating fractures of the femur comprising:
    an intramedullary rod having a longitudinal axis and defining a coaxial bore therethrough, said rod having a proximal head and a stem distal thereto, and being adapted in use for insertion into the marrow canal of a femur;
    said stem having at least one pair of stem holes, both holes of said at least one pair of stem holes being coaxially arranged on a common axis extending through said bore in a transverse direction relative to the longitudinal axis of said rod;
    said head having at least a distal pair of head holes and a proximal pair of head holes, both holes of each said distal and proximal pairs of head holes being coaxially arranged on a common axis extending through said bore in an angled direction relative to the longitudinal axis of said rod such that when said rod is in position within the marrow canal of the femur said axes of said distal and proximal head holes are directed toward the head of the femur, said common axes of said distal and proximal pairs of head holes being generally parallel to each other; and
    a screw for insertion through said distal pair of head holes, said screw having a threaded surface formed at the end adapted in use to engage the head of the femur and a smooth surface formed on the remaining major portion of its length, said smooth surface being adapted in use for continuous sliding contact with said head of said rod through said distal pair of head holes to permit sliding compression of selected fractures.

2. The apparatus recited in claim 1 further comprising:
    first anchoring means adapted in use to pass through the femur and said pair of stem holes to secure said rod within the marrow canal of the femur.

3. The apparatus recited in claim 1 further comprising:
    second anchoring means adapted in use to be optionally insertable through a portion of the femur and said proximal pair of head holes to prevent rotation of the head of the femur, said second anchoring means having a threaded portion and a smooth portion for continuous sliding contact with said rod through said proximal pair of head holes.

4. The apparatus recited in claim 1 further comprising:
    a set screw adapted in use to be optionally insertable into the portion of said bore in said head to wedgedly engage said screw when said screw is inserted through said distal pair of head holes to secure the position of said screw relative to said rod.

5. The apparatus recited in claim 1 wherein there are two pairs of stem holes and said common axes of said pairs of stem holes are generally parallel to each other, said apparatus further comprising two first anchoring means, each said first anchoring means adapted in use to pass through the femur and one of said pair of stem holes to secure said rod within the marrow canal of the femur.

6. The apparatus recited in claim 1 wherein the diameter of said distal pair of head holes is greater than the diameter of said proximal pair of head holes.

7. The apparatus recited in claim 1 wherein said bore has a closed cross section along its entire length and the exterior cross section of said rod is scalloped and the interior cross section resembles a cloverleaf in shape.

8. The apparatus recited in claim 1 wherein said longitudinal axis curves in at least one portion of said stem through one plane to align said rod along the length of the marrow canal of the femur when said rod is inserted in the femur.

9. The apparatus recited in claim 1 wherein said screw includes means for permitting said screw to be tightened relative to said rod to compress a fracture.

10. The apparatus recited in claim 1 wherein said screw is cannulated to permit insertion of a guide wire.

* * * * *